United States Patent [19]

Givens et al.

[11] 4,079,096

[45] Mar. 14, 1978

[54] MANUFACTURE OF LIGHT OLEFINS

[75] Inventors: Edwin N. Givens, Pitman; Charles J. Plank, Woodbury; Edward J. Rosinski, Pedricktown, all of N.J.

[73] Assignee: Mobil Oil Corporation, New York, N.Y.

[21] Appl. No.: 738,773

[22] Filed: Nov. 4, 1976

[51] Int. Cl.$^2$ .............................................. C07C 1/24
[52] U.S. Cl. .................................................... 260/682
[58] Field of Search ........................................ 260/682

[56] References Cited

U.S. PATENT DOCUMENTS 3,979,472  9/1976  Butter ................................... 260/682

Primary Examiner—Delbert E. Gantz
Assistant Examiner—C. E. Spresser
Attorney, Agent, or Firm—Charles A. Huggett; Raymond W. Barclay

[57] ABSTRACT

A catalytic process is provided for converting a charge consisting essentially of methanol, dimethyl ether or mixtures thereof to a hydrocarbon product rich in ethylene and propylene by contact, under conversion conditions, with a catalyst comprising the crystalline aluminosilicate zeolite designated "ZSM-34".

12 Claims, No Drawings

MANUFACTURE OF LIGHT OLEFINS

CROSS-REFERENCE TO RELATED APPLICATIONS

ZSM-34 as a new crystalline aluminosilicate zeolite, its method of preparation and hydrocarbon conversion in the presence thereof are described in copending application Ser. No. 738,771, filed concurrently herewith.

BACKGROUND OF THE INVENTION

1. Field of the Invention

This invention relates to a process for the conversion of methanol, dimethyl ether or mixtures thereof to light olefins in the presence of a specified crystalline aluminosilicate zeolite-containing catalyst.

2. Description of the Prior Art

U.S. Pat. No. 3,036,134 to Mattox discloses conversion of methanol to a reaction product containing water and dimethyl ether in the presence of a sodium or calcium crystalline aluminosilicate zeolite catalyst.

U.S. Pat. No. 3,529,033 to Frilette and Weisz discloses dehydration of a normal alkanol of three to six carbon atoms to an olefin, utilizing a sodium or calcium crystalline aluminosilicate zeolite catalyst having uniform interstitial dimensions sufficiently large to admit the alkanol charge and to permit egress therefrom of the olefin product.

The prior art, typified by the above patents, has neither disclosed nor recognized the advantages of a process for selectively converting methanol, dimethyl ether or mixtures thereof to $C_2$-$C_3$ olefins utilizing the crystalline aluminosilicate zeolite catalyst described herein.

As those in the art are aware, a remarkable growth in the production of synthetic fibers, plastics and rubber has taken place in recent decades. Their growth, to a very large extent, has been supported and encouraged by an expanding supply of inexpensive petroleum raw materials such as ethylene and propylene. Increasing demand for these light olefins has, from time to time, led to periods of shortage, either due to a diminished supply of suitable feedstocks or to limited processing capacity. In any event, it is considered highly desirable to provide efficient means for converting raw materials other than petroleum to light olefins.

SUMMARY OF THE INVENTION

In accordance with the present invention, there has been discovered a process which selectively produces valuable light olefinic hydrocarbons. The present process involves conversion of methanol, dimethyl ether or mixtures thereof by contact at elevated temperatures with a catalyst comprising the crystalline aluminosilicate zeolite ASM-34.

It has been found that use of such zeolite catalyst affords a substantially higher selectivity for ethylene and propylene production over corresponding use of other crystalline aluminosilicate zeolites. It has further been found utilizing the specified crystalline aluminosilicate zeolite catalyst described herein that the $C_2$-$C_3$ olefin content of the reaction product obtained can be in excess of 35 weight percent and preferably constitute a major proportion of such reaction product. The latter is substantially devoid of aromatic hydrocarbon content and contains, as a result of employing the specified catalyst, less than 20 weight percent, and preferably not more than 10 weight percent, of methane.

The methanol feedstock may be manufactured from synthesis gas, i.e., a mixture of CO and $H_2$, from coal or may be produced by fermentation.

The present process comprises conversion of methanol, dimethyl ether or mixtures thereof in the presence of the specified catalyst at a temperature between about 500° F and about 1000° F at a pressure between about 0.1 and about 30 atmospheres and preferably at atmospheric pressure utilizing a weight hourly space velocity (WHSV) between about 0.1 and about 30 and preferably between about 1 and about 10, said operating conditions being selected to produce olefins boiling below C5 hydrocarbons. The WHSV is based upon the weight of zeolite in the catalyst composition. The effluent is separated and distilled to remove the desired products of light olefinic hydrocarbons. Any unreacted charge may be recycled for further reaction.

DESCRIPTION OF SPECIFIC EMBODIMENTS

It is contemplated that methyl alcohol, dimethyl ether or mixtures thereof may be used as feed to the process of this invention. Such feed, in accordance with this invention, is brought into contact, under the aforenoted conversion conditions, with a bed comprising particle-form catalyst containing the crystalline aluminosilicate zeolite ZSM-34.

The latter zeolite and its synthesis are subject matter of copending application Ser. No. 738,771, filed Nov. 4, 1976, the contents of which are incorporated herein by reference. ZSM-34 is a unique crystalline aluminosilicate zeolite, belonging to the erionite-offretite family, having the composition, as synthesized, and after drying of:

$$(0.5\text{-}1.3)R_2O : (0\text{-}0.15) Na_2O : (0.10\text{-}0.50) K_2O : Al_2O_3 : X\ SiO_2$$

where R is the organic nitrogen-containing cation derived from choline 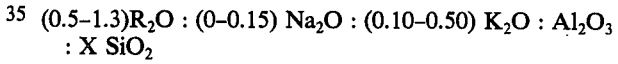 and X is 8 to 50, preferably 8 to 30 and still more preferably 8 to 20. This zeolite, unlike other members of the erionite-offretite family, appears to have a tabular morphology and the capability, after calcination at 1000° F for at least a period of time to remove the organic cation, of sorbing at least 9.5 weight percent of n-hexane at ambient temperature and a n-hexane pressure of 20 mm, which is higher than that for any other known offretite or erionite.

ZSM-34 is characterized by an X-ray powder diffraction pattern as set forth in Table 1 below:

TABLE 1

| ° 2θ | D(A) | Relative Intensity |
|---|---|---|
| 7.68 | 11.5 ± .2 | VS |
| 9.62 | 9.2 ± .2 | W |
| 11.67 | 7.58 ± .15 | M |
| 13.39 | 6.61 ± .13 | S |
| 14.01 | 6.32 ± .12 | W |
| 15.46 | 5.73 ± .11 | M |
| 16.57 | 5.35 ± .10 | W |
| 17.81 | 4.98 ± .10 | W |
| 19.42 | 4.57 ± .09 | S-VS |
| 20.56 | 4.32 ± .08 | VS |
| 21.36 | 4.16 ± .08 | W |
| 23.35 | 3.81 ± .07 | S-VS |
| 23.79 | 3.74 ± .07 | VS |
| 24.80 | 3.59 ± .07 | S-VS |
| 27.02 | 3.30 ± .06 | M-S |
| 28.33 | 3.15 ± .06 | M |
| 30.62 | 2.92 ± .05 | W |
| 31.41 | 2.85 ± .05 | VS |
| 31.93 | 2.80 ± .05 | W |
| 33.50 | 2.67 ± .05 | W |

TABLE 1-continued

| °2θ | D(A) | Relative Intensity |
|---|---|---|
| 35.68 | 2.52 ± .05 | W |
| 36.15 | 2.48 ± .05 | W-M |
| 38.30 | 2.35 ± .04 | W |
| 39.49 | 2.28 ± .04 | W |

The intensity in the above table is expressed as follows:

| Relative Intensity | 100 I/Io |
|---|---|
| VS (Very Strong) | 60-100 |
| S (Strong) | 40-60 |
| M (Medium) | 20-40 |
| W (Weak) | 0-20 |

This zeolite, as synthesized, may be calcined to remove the organic constituent ($R_2O$) and/or ion exchanged to replace the alkali metal ions with hydrogen ion precursor and/or other metal ions, particularly metals from Groups IB, II, III, VIIB, VIII and the rare earth metals with only minor changes in the X-ray characterization and sorption properties. The calcined and ion exchanged product is catalytically active ZSM-34 useful in the process of this invention.

ZSM-34 can be suitably synthesized by preparing a gel reaction mixture having a composition, in terms of mole rations of oxides, falling within the following ranges:

| | Broad | Preferred |
|---|---|---|
| $SiO_2/Al_2O_3$ = | 10-70 | 10-55 |
| $OH^-/SiO_2$ = | 0.3-1.0 | 0.3-0.8 |
| $H_2O/OH$ = | 20-100 | 20-80 |
| $K_2O/M_2O$ = | 0.1-1.0 | 0.1-1.0 |
| $R^+/R^++M^+$ = | 0.1-0.8 | 0.1-0.5 | where $R^+$ is choline $[(CH_3)_3.N-CH_2CH_2OH]$ and M is Na+K and maintaining the mixture until crystals of the zeolite are formed. $OH^-$ is calculated from inorganic base not neutralized by any added mineral acid or acid salt. Resulting zeolite crystals are separated and recovered. Typical reaction conditions consist of heating the foregoing reaction mixture to a temperature of from about 80° C to about 175° C for a period of time of from about 12 hours to about 200 days. A more preferred temperature range is from about 90° C to about 160° C with the amount of time at a temperature in such range being from about 12 hours to 50 days.

The resulting crystalline product is separated from the mother liquor by filtration, water washing and drying, e.g. at 230° F for from 4 to 48 hours. Milder conditions may be employed, if desired, e.g., room temperature under vacuum.

ZSM-34, when employed either as an absorbent or as a catalyst in a hydrocarbon conversion process, should be at least partially dehydrated and the organic cation at least partially removed. This can be done by heating to a temperature in the range of 200° to 750° C in an atmosphere such as air, nitrogen, etc. and at atmospheric or subatmospheric pressure for between 1 and 48 hours. Dehydration can also be performed at lower temperatures merely by placing the catalyst in a vacuum, but a longer time is required to obtain a sufficient amount of dehydration.

The composition of ZSM-34 can be prepared utilizing materials which supply the appropriate oxide. Such compositions include, for example, sodium aluminate, alumina, sodium silicate, silica hydrosol, silica gel, silicic acid, sodium hydroxide, aluminum sulfate, potassium hydroxide, potassium silicate, and choline. It will be understood that each oxide component utilized in the reaction mixture for preparing ZSM-34 can be supplied by one or more initial reactants and they can be mixed together in any order. The reaction mixture can be prepared either batchwise or continuously. Crystal size and crystallization time of the ZSM-34 composition will vary with the nature of the reaction mixture employed.

The ZSM-34 useful in the conversion process of this invention generally has at least 10 percent of the cationic sites thereof occupied by ions other than alkali or alkaline earth metals. Replacement of the original ions is generally accomplished by ion exchange, preferably after calcination. Typical but nonlimiting replacing ions include ammonium, hydrogen, rare earth, zinc, copper, nickel and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g. ammonium ions, which upon calcination yield the hydrogen form. This exchange is conveniently carried out by contact of the zeolite with an ammonium salt solution, e.g., ammonium chloride, utilizing well known ion exchange techniques. The extent of replacement is such as to produce a zeolite material in which at least 50 percent of the cationic sites are occupied by hydrogen ions.

In some instances, it has been found desirable to subject the ion-exchanged zeolite to steam treatment for 1 to about 100 hours at a temperature above about 700° F but less than about 1200° F.

In practicing the desired conversion process, it may be desirable to incorporate the above-described crystalline aluminosilicate zeolite in another material resistant to the temperature and other conditions employed in the process. Such matrix materials include synthetic or naturally occurring substances as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the ZSM-34 zeolite employed herein may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The process of this invention is conducted such that methyl alcohol and/or dimethyl ether conversion is carried out in the vapor phase by contact in a reaction zone, such as for example, a fixed bed of catalyst, under effective conversion conditions. Such conditions include an operating temperature between about 500° F, and about 1000° F, a pressure between about 0.1 and about 30 atmospheres and preferably atmospheric pressure and a weight hourly space velocity between about 0.1 and about 30 and preferably between about 1 and about 10. Carrier gases or diluents may be injected into the reaction zone such as, for example, hydrogen, carbon monoxide, carbon dioxide or nitrogen.

The methyl alcohol and/or dimethyl ether conversion process described herein may be carried out as a batch-type semi-continuous or continuous operation utilizing a fixed, fluidized or moving bed catalyst system. A preferred embodiment entails use of a catalyst zone wherein the alcohol or ether charge is passed concurrently or countercurrently through a moving or fluidized bed of particle-form catalyst. The latter after use is conducted to a regeneration zone wherein coke is burned from the catalyst in an oxygen-containing atmosphere, e.g., air, at an elevated temperature, after which the regenerated catalyst is recycled to the conversion zone for further contact with the alcohol and/or ether feed.

The product stream in the process of the invention contains steam and a hydrocarbon mixture of paraffins and olefins, substantially devoid of aromatics. This mixture is particularly rich in light olefins, i.e., ethylene and propylene. Generally, a major fraction of the total olefins is ethylene plus propylene, with the ethylene content of the product exceeding the propylene content. Thus, the predominant hydrocarbon product constitutes valuable petrochemicals. The steam and hydrocarbon products may be separated from one another by methods well known in the art.

The following examples will serve to illustrate the process of this invention without limiting the same.

EXAMPLE 1

ZSM-34 was prepared by interacting the following solutions:

A. Caustic Aluminate Solution
 22.96 grams $NaAlO_2$ (43.1 wt % $Al_2O_3$, 33.1 wt % $Na_2O$, 23.8 wt % $H_2O$)
 9.76 grams NaOH (97.5%)
 8.8 grams KOH (86.4%)
 180 grams $H_2O$
B. Colloidal Silica
 260 grams (30 wt % $SiO_2$)
C. Choline Chloride
 76 grams These solutions were mixed together by adding C to A then adding B and mixing for 15 minutes. The mixture was transferred to a polypropylene container and reacted at 210° F for 32 days yielding a zeolite identified as ZSM-34.

A sample of the above alkali zeolite after filtering, washing and drying had the following molar composition:

$0.07\ Na_2O : 0.36\ K_2O : 0.67\ R_2O : Al_2O_3 : 10.2\ SiO_2$ where R is the organic ion derived from choline chloride.

The adsorption capacity for a sample of the above product calcined (16 hrs. at 1000° F) was:
Cyclohexane, wt %:4.9
n-Hexane, wt %:10.3
$H_2O$, wt %:20.9
The surface area for the calcined sample was 524 m²/g.

Another sample of the above alkali product was processed by calcining for 10 hours at 1000° F and exchanged with a 10 wt % $NH_4Cl$ solution at 185° F employing 5 one hour contacts. After the final contact the exchanged product was filtered, water washed, dried at 230° F, pelleted and sized 14–25 mesh and calcined for 10 hours at 100° F in air.

EXAMPLE 2

Methanol at a flow rate of 3.85 ml/hr was passed over 1.0 gram of the ion exchanged catalyst product of Example 1 at atmospheric pressure and a nominal 700° F. The catalyst bed had an axial bed length of 2⅜ inches. The catalyst was pretreated in place with an air flow of 10 cc/min at 1000° F for 1 hour followed by a 10 minute nitrogen purge of 10 cc/min while the reactor temperature dropped to 700° F. When methanol was passed over the bed, the temperature profile of the bed changed as shown in Table 2 after 2 hours on stream. The effluent stream from the reactor was collected between 1 and 2 hours on stream. Run conditions and product analysis are shown in Table 3. In this example, 87.9% of the methanol was converted of which 21% went to an oxygen-free hydrocarbon product. This product was 50.9% ethylene and 27.3% propylene.

EXAMPLE 3

Dimethyl ether (DME) was passed over 1.0 gram of the ion exchanged catalyst product of Example 1 at a rate of 2.0 liters per hour at a nominal 700° F. The catalyst bed had an axial bed length of 2⅜ inches. The catalyst was pretreated in place with an air flow of 10 cc/min at 1000° F for 1 hour followed by a 10 min. nitrogen purge during which the temperature dropped to 700° F. DME was then passed over the bed. The temperature profiles of the catalyst bed after 2 and 6 hours on stream are shown in Table 2. The effluent stream from the reactor was collected between 1 and 2 hours and between 5 and 6 hours on stream. The run conditions and product analyses are shown in Table 3. Between 1-2 hours on stream 39.5% of the charged DME was converted of which 54.2% went to hydrocarbons (oxygen-free). Ethylene was 22.0% of the hydrocarbon phase and propylene was 15.3%.

EXAMPLE 4

The catalyst used in Example 3 was calcined in situ for 16 hours to burn off residual carbon at 1000° F in an air flow of 10 cc/min. The bed was purged with nitrogen at a flow of 10 cc/min for 10 minutes while the temperature dropped to 700° F. Methanol at a rate of 4.0 ml/hr was passed over the bed at a nominal 700° F. The temperature profiles (Table 2) of the bed were taken at 2 and 5.5 hours on stream. The effluent stream from the reactor was collected between 1 and 2 hours and 4.5 and 5.5 hours on stream. The run conditions and product analyses are shown in Table 3.

EXAMPLE 5

Methanol at a flow rate of 3.75 ml/hr was passed over 1.0 gram of the ion exchanged catalyst product of Example 1 which had been steamed for 20 hours at 900° F. The catalyst at a nominal 700° F and atmospheric pressure was contained in a reactor with an axial bed length of 2¼ inches. The catalyst was pretreated in place with an air flow of 10 cc/min at 1000° F for one hour followed by a 10 minute nitrogen purge of 10 cc/min while the reactor temperature dropped to 700° F. When methanol was passed over the bed, the temperature profile of the bed changed as shown in Table 2 after 2 hours on stream. The effluent stream from the reactor was collected between 1 and 2 hours on stream.

The run conditions and product analysis are shown in Table 3. In this 87.2% of the methanol was converted of which 17.8% went to an oxygen-free hydrocarbon product. This product was 54.6% ethylene and 29.4% propylene.

EXAMPLE 6

Addition of steam as a diluent improved the selectivity for ethylene. A charge solution comprised of 30% by wt of methyl alcohol and 70% by wt of water was passed over 1.0 gram of the catalyst from Example 4 at a rate of 3.6 grams per hour. The run was made at a nominal 700° F and atmospheric pressure. The catalyst bed had an axial bed length of 2½ inches. The catalyst from Example 4 was calcined in place with an air flow of 10 cc/min at 1000° F for 5 hours followed by a 10 minute nitrogen purge of 10 cc/min while the reactor temperature dropped to 700° F. The temperature distribution of the bed after passing charge for two hours is shown in Table 2. The effluent stream from the reactor was collected between 1 and 2 hours on stream. Run conditions and product analysis are shown in Table 4. In the run 72.2% of the methyl alcohol was converted of which 41.4% went to oxygen-free hydrocarbon product. The selectivity for ethylene was 59.7%.

TABLE 2

| Example No. | 2 | 3 | 3 | 4 | 4 | 5 | 6 |
|---|---|---|---|---|---|---|---|
| Hours on Stream | 2 | 2 | 6 | 2 | 5.5 | 2 | 2 |
| Axial Length of Bed (inches) | 2-3/8 | 2-7/16 | 2-7/16 | 2-7/16 | 2-7/16 | 2-1/4 | 2-1/2 |
| Temp., ° F. (inches from top) | | | | | | | |
| 0 | 638 | 674 | 675 | 682 | 685 | 682 | 660 |
| 1/2 | 688 | 696 | 692 | 694 | 698 | 698 | 697 |
| 1 | 698 | 703 | 698 | 698 | 700 | 695 | 703 |
| 1-1/2 | 693 | 700 | 699 | 698 | 696 | 700 | 701 |
| 2 | 687 | 708 | 705 | 707 | 706 | 714 | 710 |
| 2-3/8 | 692 | | | | | | |
| 2-7/16 | | 715 | 716 | 712 | 718 | | |
| 2-1/2 | | | | | | 715 | 721 |

TABLE 3

| | Example 2 | Example 3 | Example 3 | Example 4 | Example 4 | Example 5 |
|---|---|---|---|---|---|---|
| Charge | MeOH | DME | DME | MeOH | MeOH | MeOH |
| Hours on Stream | 2 | 2 | 6 | 2 | 5.5 | 2 |
| Temp., ° F (nominal) | 700 | 700 | 700 | 700 | 700 | 700 |
| WHSV (on Recovered) | 2.9 | 3.1 | 3.3 | 2.0 | 3.0 | 3.0 |
| Conversion of CHg, Wt % | 87.9 | 39.5 | 11.9 | 88.2 | 85.9 | 87.2 |
| Product (Wt. %): | | | | | | |
| MeOH | — | 22.9 | 26.3 | — | — | — |
| DME | 31.2 | — | — | 36.9 | 56.8 | 39.9 |
| Water | 47.5 | 22.6 | 11.0 | 40.3 | 34.4 | 41.9 |
| Hydrocarbon Phase | 21.0 | 54.2 | 62.7 | 22.4 | 8.6 | 17.8 |
| Hydrocarbon Distribution Wt % | | | | | | |
| $C_1$ | 2.4 | 2.0 | 2.6 | 2.1 | 2.3 | 2.9 |
| $C_2=$ | 50.9 | 22.0 | 16.0 | 42.5 | 25.6 | 54.6 |
| $C_2$ | 0.5 | 0.2 | 0 | 0.4 | 0 | 0.7 |
| $C_3=$ | 27.3 | 15.3 | 8.0 | 26.1 | 17.6 | 29.4 |
| $C_3$ | 0.3 | 2.4 | 4.8 | 1.8 | 2.1 | 1.8 |
| $C_4=$ | 8.7 | 9.8 | 13.7 | 6.7 | 5.4 | 6.2 |
| $C_4$ | 4.1 | 8.7 | 7.9 | 3.8 | 1.9 | 1.4 |
| $C_5+$ | 5.8 | 39.4 | 47.0 | 16.5 | 45.1 | 2.5 |

TABLE 4

| | Example 6 |
|---|---|
| Charge: | MeOH/$H_2O$ |
| Hours on Stream | 2 |
| Temp., ° F (nominal) | 700 |
| WHSV (Total) | 3.6 |
| of MeOH | 1.2 |
| of Water | 2.4 |
| Mole Ratio ($H_2O$/MeOH) | 3.4/1 |
| Conversion of MeOH, wt % | 72.2 |
| Product (wt %) | |
| DME | 3.9 |
| Water (excludes water in charge) | 54.7 |
| Hydrocarbon Phase | 41.4 |
| Hydrocarbon Phase (Wt %) | |
| $C_1$ | 1.6 |
| $C_2=$ | 59.7 |
| $C_2$ | 1.1 |
| $C_3=$ | 23.6 |
| $C_3$ | 5.2 |
| $C_4=$ | 5.8 |
| $C_4$ | 1.3 |
| $C_5=$ | 1.4 |
| $C_5$ | 0.3 |

EXAMPLE 7

A 603 gram sample of 14 × 25 mesh ion-exchanged ZSM-34 prepared as in Example 1 was calcined for 10 hours at 1000° F. and then evacuated for ½ hour. Thereafter, the sample was contacted by shaking with 6.3 ml. of Zn(NO$_3$)$_2$ solution containing 0.291 gram Zn(NO$_3$)$_2$·6H$_2$O (0.0636 gram Zn) to introduce about 1 weight percent of zinc. The resulting composite was then dried at 230° F. and calcined for 10 hours at 1000° F. On analysis, the catalyst contained 0.96 weight percent zinc.

Methanol at a rate of 3.8 ml. per hour was passed over 1 gram of the above catalyst. The catalyst was air calcined in place at 1000° F. for one hour with an air flow of 10 cc/minute. Nitrogen at a rate of 10 cc/minute was passed over the bed for 10 minutes while the temperature dropped to 700° F. The run conditions, temperature profile of the bed and product analysis of the reactor effluent collected between 1 and 2 hours on stream are set forth in Table 5 below:

TABLE 5

| Example No. | 7 |
|---|---|
| Charge: wt% MeOH | 100 |
| Axial Length of Bed in inches | 2 ¼ |
| Reactor Diameter (mm OD) | 8 |
| Temp. Profile  0 | 679 |
| Inches from top  ½ | 705 |
| 1 | 705 |
| 1½ | 697 |
| 2 | 710 |
| Hrs. on Stream of Temp. Profile | 2 |
| WHSV | 3.0 |
| Converted MeOH (wt. %) | 88.7 |
| Products (charge free) wt % | |
| Water | 38.2 |
| DME | 42.0 |
| HC Phase | 19.5 |
| HC Phase Composition (wt %) | |
| $C_1$ | 2.6 |
| $C_2=$ | 45.2 |
| $C_2$ | 0.4 |
| $C_3=$ | 26.8 |
| $C_3$ | 0 |
| $C_4=$ | 6.5 |
| $C_4$ | 2.9 |
| $C_5+$ | 15.5 |

It will be evident that of the 88.7 percent methanol converted, 19.5 percent went to oxygen-free hydrocarbon product, with an ethylene content of 45.2 weight percent.

EXAMPLE 8

This example was prepared as described below:

Zeolite Synthesis

The following solutions were prepared:

A. Caustic Aluminate
  68.89 grams sodium aluminate (20 wt % Na, 43.1 wt % $Al_2O_3$ Balance $H_2O$)
  29.28 grams NaOH (77.5 wt % $Na_2O$)
  26.4 grams KOH 86.4 wt % KOH
  540 grams $H_2O$
B. Silica Solution
  780 grams Colloidal Silica sol (30 wt % $SiO_2$)
C. Choline Chloride
  222 grams These were mixed together in a 2 liter autoclave adding solution C to solution A and then adding solution B followed by a 15 minute continuous mixing. The autoclave was then sealed, pressure-tested and then heated to and held at 300° F for 8 days. The contents were stirred continuously during the 8 day crystallization period.

The autoclave and its contents were cooled to room temperature and the crystalline product was filtered and washed. On analysis the product was found to contain:
  Na, wt % : 0.68
  K, wt % : 3.59
  $Al_2O_3$, wt % : 13.5
  $SiO_2$, wt % : 78.5
  N, wt % : 2.0

The resulting ZSM-34 product has the following molar composition:

$0.54\ R_2O : 0.11\ Na_2O : 0.35\ K_2O : Al_2O_3 : 9.87\ SiO_2$

The adsorption data for the product after calcining in air at 1000° F for 10 hours was as follows:
  Cyclohexane wt % : 3.5
  n-Hexane, wt % : 9.6
  $H_2O$, wt % : 19.7

A sample of the above calcined alkali ZSM-34 was further processed by contacting with a 10 wt % $NH_4Cl$ solution for 1 hour at about 185° F using 10 ml of solution for each gram of ZSM-34. A total of four contacts were made at these conditions followed by final filtration and water washing essentially free of chloride ion.

The product was dried at 230° F and calcined for 10 hours at 1000° F. The residual alkali content as Na was 0.035 wt % while the residual K content was 1.47 wt %. This product had a surface area of 517 $m^2/g$ and the following sorption capacity:
  Cyclohexane, wt % : 2.6
  n-Hexane, wt % : 10.0
  $H_2O$, wt % : 18.7

EXAMPLE 9

A feed comprised of 30 wt % methanol and 70 % water was passed over 2.0 g of the catalyst of Example 8 at a rate of 7.7 ml per hour. The catalyst contained in a 15 mm OD tubular glass reactor, had an axial bed length of 1 ⅝ inches. The catalyst was air calcined in place at 1000° F for one hour with an air flow of 10 cc/min. Nitrogen at a rate of 10 cc/min was passed over the bed for 10 min while the temperature dropped to 700° F. The run conditions, temperature profile of the bed and the product analysis of reactor effluent samples taken at four different intervals during the run are set forth in Table 6 below:

TABLE 6

| Hours on Stream | | 1–2 | 4.5–5.5 | 7–8 | 11–12 |
|---|---|---|---|---|---|
| Temp., ° F  0 | | 655 | 645 | 638 | 654 |
| (inches from Top) | ½ | 693 | 682 | 687 | 693 |
| | 1 | 700 | 693 | 702 | 705 |
| | 1½ | 705 | 706 | 723 | 725 |
| | 1⅝ | 706 | 716 | 730 | 735 |
| Temp. profile, Hrs. | | 2 | 5.5 | 8 | 12 |
| Calculations on Recovered: | | | | | |
| WHSV Total | | 3.6 | 3.6 | 2.9 | 2.9 |
| MeOH | | 0.86 | 1.0 | 0.81 | 0.76 |
| Water | | 2.7 | 2.6 | 2.1 | 2.1 |
| Converted MeOH (wt %) | | 96.0 | 65.4 | 37.1 | 33.8 |
| Product (excludes unreacted charge) wt % | | | | | |
| DME | | 1.9 | 19.3 | 47.2 | 57.2 |
| Water | | 55.5 | 48.7 | 37.8 | 33.8 |
| HC Phase | | 42.6 | 32.0 | 15.0 | 8.9 |
| HC Distribution (wt %) | | | | | |
| $C_1$ | | 3.0 | 4.9 | 7.5 | |
| $C_2=$ | | 48.8 | 56.0 | 52.9 | 53.7 |
| $C_2$ | | 1.8 | 0.4 | 0 | 0 |
| $C_3=$ | | 26.8 | 27.2 | 27.7 | 25.8 |
| $C_3$ | | 7.1 | 0 | 0 | 0 |
| $C_4=$ | | 7.8 | 6.5 | 6.5 | 6.0 |
| $C_4$ | | 3.3 | 4.7 | 3.6 | 4.5 |
| $C_5$ | | 2.6 | 2.2 | 4.5 | 2.6 |

It will be seen from the above data that use of ZSM-34 in conversion of methanol afforded exceptionally high selectivity for ethylene and propylene. Dimethyl ether converted in the presence of this catalyst also gave good yields of ethylene, although somewhat lower than for methanol. Introduction of steam to the methanol feed served to improved the overall selectivity for ethylene.

It is to be understood that the foregoing description is merely illustrative of preferred embodiments of the invention of which many variations may be made by those skilled in the art within the scope of the following claims without departing from the spirit thereof.

We claim:

1. A catalytic process for converting a charge consisting essentially of methanol, dimethyl ether or mixtures thereof to a hydrocarbon product rich in ethylene and propylene which comprises contacting said charge under conversion conditions including a temperature between about 500° F and about 1000° F, a pressure from about 0.1 to 30 atmospheres and a weight hourly space velocity of between about 0.1 and about 30 with a catalyst comprising the crystalline aluminosilicate zeolite ZSM-34.

2. The process of claim 1 wherein ethylene and propylene constitute a major proportion of the hydrocarbon reaction product.

3. The process of claim 2 wherein the ethylene content of said product exceeds the propylene content.

4. The process of claim 1 wherein the amount of ethylene and propylene produced is in excess of 35 weight percent and the amount of methane produced is not more than 10 weight percent of the hydrocarbon reaction product.

5. The process of claim 1 wherein said charge is methanol.

6. The process of claim 1 wherein said crystalline aluminosilicate has been thermally treated at a temperature of from about 200° C to about 750° C.

7. The process of claim 6 wherein at least 10 percent of the cationic sites of said crystalline aluminosilicate are occupied by ions other than alkali or alkaline earth metals.

8. The process of claim 7 wherein said ions are hydrogen, hydrogen precursors, metals from Groups IB, II, III, VIIB, VIII or rare earth metals.

9. The process of claim 7 wherein said ions are ammonium, hydrogen, rare earth or combinations thereof.

10. The process of claim 1 wherein said crystalline aluminosilicate zeolite is predominantly in the hydrogen form.

11. The process of claim 1 wherein said crystalline aluminosilicate zeolite is contained in a matrix therefor.

12. The process of claim 7 wherein said crystalline aluminosilicate has been subjected to steam treatment for 1 to about 100 hours at a temperature above about 700° F but less than about 1200° F.

* * * * *

UNITED STATES PATENT AND TRADEMARK OFFICE
CERTIFICATE OF CORRECTION

PATENT NO. : 4,079,096

DATED : March 14, 1978

INVENTOR(S) : EDWIN N. GIVENS, CHARLES J. PLANK and EDWARD J. ROSINSKI

It is certified that error appears in the above-identified patent and that said Letters Patent are hereby corrected as shown below:

Column 1, line 55, "ASM-34" should read --ZSM-34--.
Column 3, line 29, "rations" should read --ratios--.
Column 6, line 41, "2-3/8" should read --2-7/16--.
Column 8, Table 3, line 33, Example 5, last line, "2.5" should read --2.8--.
Column 10, Table 6, line 52, "$C_{1\ 1.8}$" should read --$C_1$--.

"3.0" should read --1.8--.
"4.9" should read --3.0--.
"7.5" should read --4.9--.
Blank space, should read --7.5--.

Signed and Sealed this

Eleventh Day of July 1978

[SEAL]

Attest:

RUTH C. MASON
Attesting Officer

DONALD W. BANNER
Commissioner of Patents and Trademarks